United States Patent [19]

Lin

[11] Patent Number: 5,512,610
[45] Date of Patent: Apr. 30, 1996

[54] BONE CEMENT COMPOSITION

[75] Inventor: Steve T. Lin, Fort Wayne, Ind.

[73] Assignee: Zimmer, Inc., Warsaw, Ind.

[21] Appl. No.: 281,326

[22] Filed: Jul. 27, 1994

Related U.S. Application Data

[63] Continuation-in-part of Ser. No. 921,030, Jul. 28, 1992, Pat. No. 5,334,626.

[51] Int. Cl.$^6$ ............................... A61K 6/08; A61F 2/00; B05D 1/36; B05D 7/00
[52] U.S. Cl. ..................... 523/116; 523/115; 523/117; 523/206; 523/207; 523/211; 427/203; 427/214; 427/222
[58] Field of Search ..................... 523/115, 116, 523/117, 206, 207, 211; 427/203, 214, 222

[56] References Cited

U.S. PATENT DOCUMENTS

| | | | |
|---|---|---|---|
| 3,715,331 | 2/1973 | Molnar | 260/41 B |
| 4,045,403 | 8/1977 | Lever et al. | 260/42.42 |
| 4,404,327 | 9/1983 | Crugnola et al. | 525/228 |
| 4,456,711 | 6/1984 | Pietsch et al. | 523/206 |
| 4,500,658 | 2/1985 | Fox | 523/117 |
| 4,535,485 | 8/1985 | Ashman et al. | 623/16 |
| 4,547,390 | 10/1985 | Ashman et al. | 427/2 |
| 4,617,327 | 10/1986 | Podszun | 523/116 |
| 4,675,140 | 6/1987 | Sparks et al. | 264/4.3 |
| 4,791,150 | 12/1988 | Braden et al. | 523/117 |
| 5,051,482 | 9/1991 | Tepic | 525/309 |
| 5,061,520 | 10/1991 | Hermelin | 427/212 |

OTHER PUBLICATIONS

Literature–Howmedica–Surgical Simplex P Bone Cement–No date available.
Literature–Zimmer–Zimmer Bone Cement–Feb. 1978.
Literature–Richards–Palacos R–No date available.
Literature–Zimmer–Chemistry of Cement Settings–No date available.

*Primary Examiner*—Paul R. Michl
*Assistant Examiner*—LaVonda R. DeWitt
*Attorney, Agent, or Firm*—Cary R. Reeves

[57] ABSTRACT

A bone cement composition has adjustable rheological properties, high strength, and produces a uniform radiological image. The cement is characterized by controlled retention and release of additives incorporated in beads included in the dry component of the cement. The cement comprises beads containing a polymerization initiator in controllable concentrations from 0% to 5% or more by weight. These same beads or others may also contain an opacifier. The polymerization initiator and the opacifier may be selectively distributed throughout the beads or at specific radial locations in the beads. They may also be selectively placed in beads of a particular advantageous size range. Furthermore, in other embodiments of the invention, other advantageous additives can be incorporated in the beads such as dyes, antibiotics, bone growth factors, and other pharmacological or therapeutic agents.

11 Claims, 2 Drawing Sheets

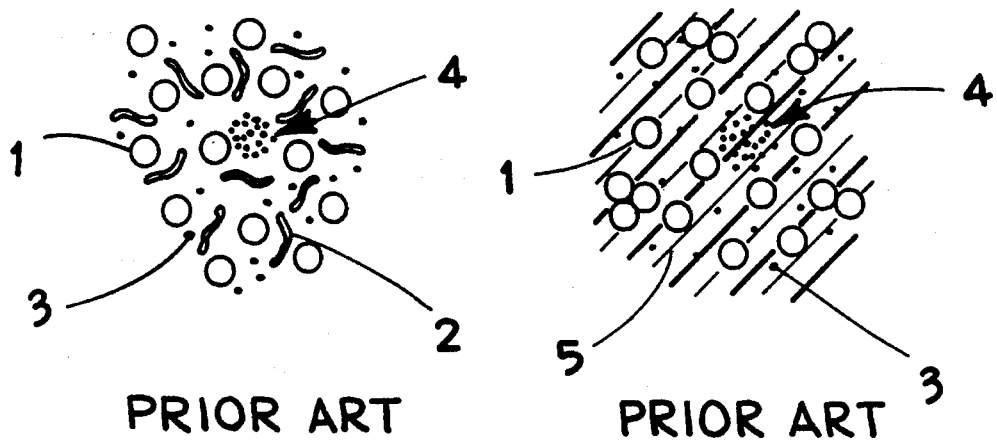
PRIOR ART
Fig. 1
PRIOR ART
Fig. 3
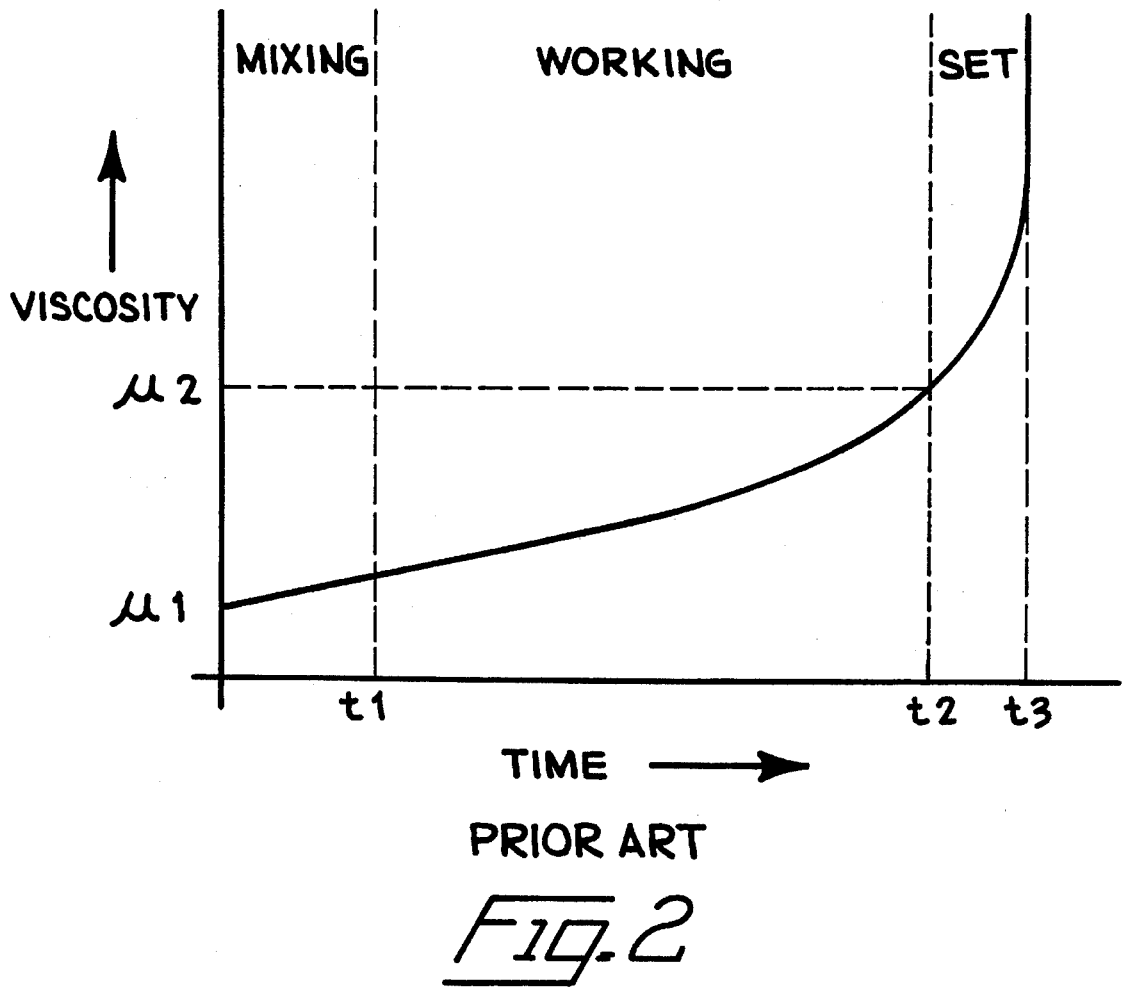
PRIOR ART
Fig. 2

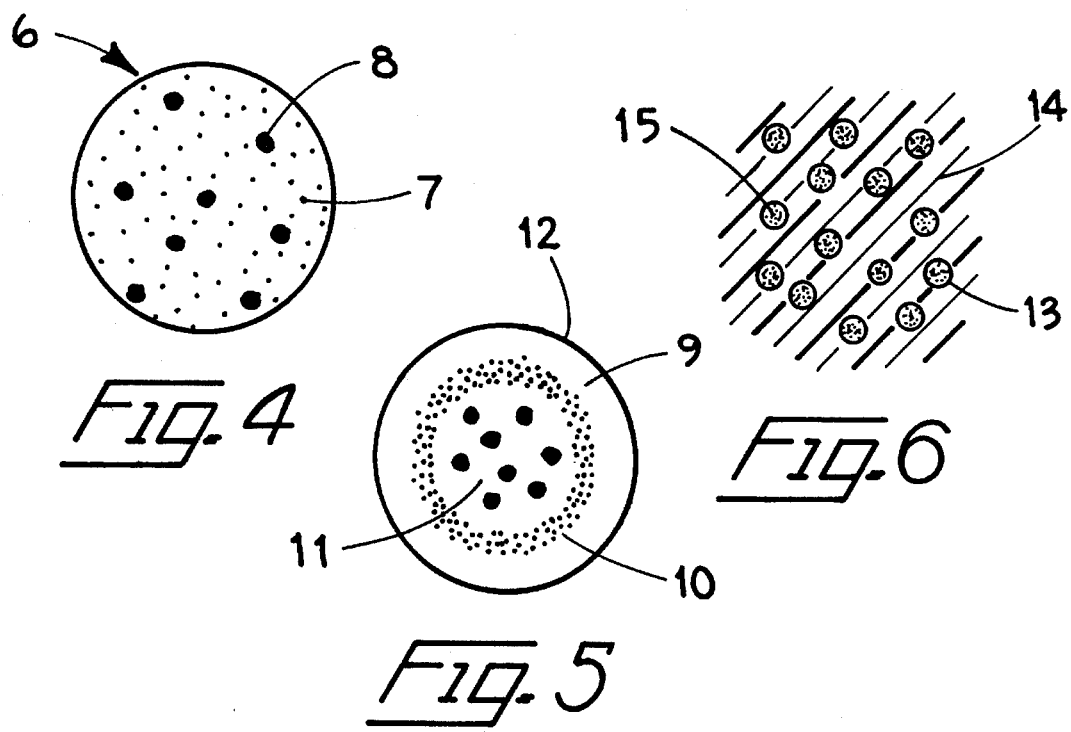
Fig. 4
Fig. 5
Fig. 6
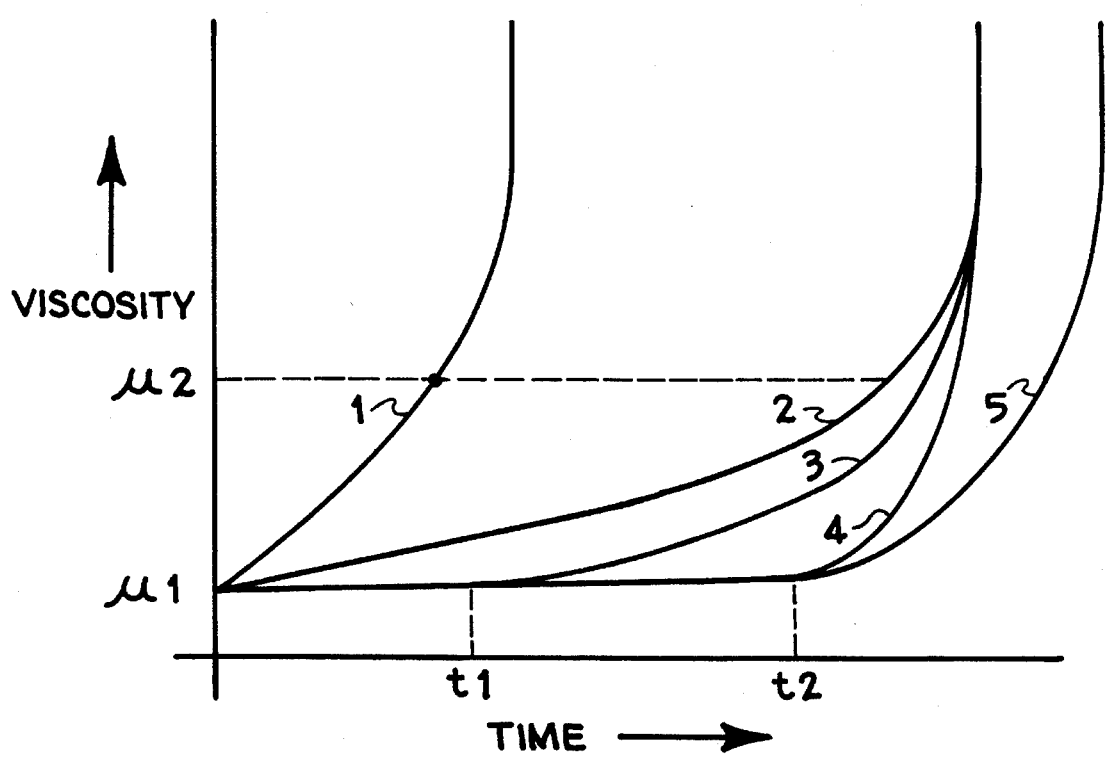
Fig. 7

BONE CEMENT COMPOSITION

CROSS-REFERENCE TO RELATED APPLICATION

This application is a continuation-in-part of application Ser. No. 07/921,030 filed Jul. 28, 1992 U.S. Pat. No. 5,334,626.

BACKGROUND OF THE INVENTION

The present invention relates to two-component plastic systems useful for surgically filling voids in bones. More specifically, the invention relates to polymer cements comprising a liquid component and a dry component wherein the dry component includes polymer beads.

Polymer based surgical cement systems have been successfully employed for many years to fill voids in bones. Such cements have found their greatest use in the fixation of orthopaedic implants. Typically a bone is cut to accommodate an implant and then liquid and dry components of the cement system are mixed to form a paste which is applied to the cut bone. The implant is seated in this paste, which, when fully polymerized, forms a continuous solid interface between the implant and bone. The invention of this disclosure encompasses improvements in these polymer bone cements. To better understand the invention, it will be helpful to review the basic composition, behavior, and deficiencies of prior cements.

FIG. 1 depicts a typical prior art dry component of a bone cement system. The dry component includes a loose mixture of polymer beads 1, polymer flakes (or milled beads) 2, and a powdered opacifier 3. The beads contain a polymerization initiator such as benzoyl peroxide (BPO). Typically these beads are formed in a solution polymerization process in which BPO is added as a polymerization initiator to a monomer and polymerization is carried out. BPO added in excess of that required for polymerization of the monomer remains in the polymer as a residual. The more BPO added, the greater will be the residual BPO randomly distributed in the polymerized beads, within practical limits. However, the molecular weight of the resulting beads decreases as the BPO is increased. A high molecular weight is important in bone cement beads because mechanical strength increases as molecular weight increases. The tradeoff between residual BPO and molecular weight has limited the residual BPO attainable in beads having a useful molecular weight. For example, it is very difficult to produce a bead with a molecular weight greater than 500,000 and a residual BPO content greater than 2% by weight. When the residual BPO content is below approximately 1% by weight, the addition of free BPO powder to the mixture comprising the dry cement component may be required to achieve a desired set time for the bone cement system. Desirable set times are typically between 10 and 15 minutes. For example U.S. Pat. Nos. 4,500,658, 4,791,150 and 4,617,327 teach the addition of free, powdered BPO as a polymerization initiator. Uniform dispersion of this BPO powder is difficult.

The opacifier 3 is included to color the cement to aid its implantation and to make it visible on a radiograph. The opacifier tends to form clumps 4 because it is a fine powder added to the beads and flakes. U.S. Pat. No. 4,791,150 to Braden et al. and U.S. Pat. No. 4,500,658 to Fox describe cements having an opacifier dispersed in polymer cement beads during the bead formation. The references teach the use of a suspension polymerization batch process for forming beads as discussed above and further teach including the opacifier particles in the suspension polymerization solution so that the beads formed will contain some opacifier. This method of incorporating opacifier is tedious and costly to use. It also produces a bead with an uncontrolled and random opacifier distribution.

In use the dry component is mixed with the liquid component which contains a monomer and typically an amine accelerator such as N,N-Dimethyl-p-toluidine (DMPT). Upon mixing, the monomer dissolves the flake polymer to a great extent due to the large surface area of the flake, thereby creating a viscous fluid or paste. In addition, the monomer begins to dissolve the beads at a much slower rate than the flake because of the relatively small surface area of the beads. As the beads partially dissolve, residual BPO becomes available to the monomer. The BPO decomposes in the presence of DMPT into free radicals which act as polymerization initiators for the monomer, and polymer chains begin forming from the beads outwardly. However, only the BPO that is exposed by bead dissolution is accessible, and the beads only partially dissolve. Therefore, since the BPO is distributed throughout the bead, the usable BPO concentration of prior art cements is less than the actual concentration in the bead. As polymerization progresses, the cement paste grows more viscous until it eventually hardens into a solid. It is helpful to characterized this hardening process as having three stages. FIG. 2 depicts a viscosity versus time graph for a typical polymer bone cement. This graph depicts the rheological behavior of the cement. During the first, or mixing stage, the cement components are mixed and a viscous paste, represented by $\mu_1$, is formed primarily due to the dissolution of the polymer flake in the monomer. During the second stage, or working time, the paste is of a suitable viscosity to be effectively applied to the bone. By design this may be a fairly thick putty-like consistency suitable for manually packing into the bone or it may be a thinner flowing consistency suitable for injection into the bone. The consistency can by controlled, for example, by varying the ratio of flake to beads in the dry component. Absent the BPO, this stage would continue for a considerable period with only slight thickening due to further dissolution of the beads. However, because of the BPO, polymerization takes place and the paste reaches a state, represented by $\mu_2$, where it is no longer able to be worked. The polymerization reaction, which is exothermic, continues during the final stage until the cement is fully randomly distributed within the beads and some of the opacifier particles will be located near the bead surface allowing the particles to become exposed and separated from the bead when the surface is dissolved by the monomer during use. Such separated particles will be deposited in the matrix and can form stress concentrators as previously described.

SUMMARY OF THE INVENTION

It is therefore an object of the present invention to provide a polymeric bone cement composition having a particularly useful viscosity versus time curve.

It is also an object of the present invention to provide a polymeric bone cement composition having improved strength due to the reduction of stress concentrating structures in the polymerized cement.

It is a further object of the present invention to provide a polymeric bone cement composition having a uniform radiographic image.

It is also an object of the present invention to provide a polymeric bone cement with advantageous additives strategically placed in controlled distributions within the cement dry component beads.

It is also an object of the present invention to provide a polymeric bone cement having beneficial additives hardened. The entire process typically takes from two to fifteen minutes. Because of the practical limits on the amount of residual BPO and its distribution throughout the beads, the viscosity versus time curve, as shown in FIG. 2, for prior art cements is not readily tailored.

The resulting solid cement, as depicted in FIG. 3, comprises a matrix of polymerized plastic 5 containing a distribution of beads 1 and opacifier 3. The beads are generally firmly attached to the matrix since the polymer chains formed from the beads outwardly as BPO was exposed. However, polymerization chains may not form from the beads uniformly if free BPO is added to raise BPO levels, as may be necessary when the residual BPO is low. In that case the dry cement component contains a non-uniform dispersion of BPO powder. When the dry cement component is mixed with the liquid cement component, polymerization will proceed more quickly at regions of relatively high BPO concentration. These regions will be outside of the beads, resulting in localized and less uniform polymerization which can result in reduced mechanical properties.

Also, the opacifier is simply encased in the matrix and forms no attachment with it thereby concentrating stresses placed on the cement and weakening it. The tendency of the opacifier to clump 4 can further weaken the cement and the clumps can obscure the radiographic image of the cement-bone interface. Where prior investigators have taught incorporation of the opacifier into the beads through solution polymerization, the opacifier will be strategically placed in particular advantageously sized cement dry component beads.

It is a still further object of the present invention to provide a method of manufacturing a polymeric bone cement composition that enables the cement's viscosity versus time curve to be readily adjusted.

It is finally an object of the present invention to provide a method of manufacturing a polymeric bone cement composition that provides for the placement of the opacifier and other additives in controlled distributions in the cement.

The above advantageous objects and others are obtained in a cement composition characterized by controlled retention and release of additives incorporated in beads included in the dry component of the cement. The cement composition comprises beads containing a polymerization initiator in controllable concentrations from 0% to 5% or more by weight. These same beads or others may also contain an opacifier. The polymerization initiator and the opacifier may be selectively distributed throughout the beads or at specific radial locations in the beads. They may also be selectively placed in beads of a particular advantageous size range. Furthermore, in other embodiments of the invention, other advantageous additives can be incorporated in the beads such as dyes, antibiotics, bone growth factors, and other pharmacological or therapeutic agents. Beads having the above described structure can be formed using a modified form of the microencapsulation technique described in U.S. Pat. No. 4,657,140 hereby incorporated by reference.

BRIEF DESCRIPTION OF THE DRAWINGS

The before mentioned features and advantages of the present invention are apparent from the following detailed description and the drawings wherein:

FIG. 1 is a schematic diagram of a prior art dry component of a polymeric cement system.

FIG. 2 is a viscosity versus time graph for a typical prior art polymeric cement system.

FIG. 3 is a schematic diagram of a prior art polymeric cement system having been fully polymerized.

FIG. 4 is a schematic diagram of a cement bead with additives distributed within it.

FIG. 5 is a schematic diagram of a cement bead with additives distributed in layers.

FIG. 6 is a schematic diagram of the inventive polymeric cement system having been fully polymerized.

FIG. 7 is a graph of several viscosity versus time curves achievable by the present inventive bone cements.

DETAILED DESCRIPTION OF THE INVENTION

Referring to FIG. 4 a polymer bead 6 has one or more additives distributed within it. The present invention provides means for selectively retaining an additive within the bead or releasing an additive from the bead. Retention and release are controlled in the present invention by the selective placement of the additive within the bead at particular locations or by the selective placement of the additive in beads of a particular size.

For example, a polymerization initiator 7, preferably benzoyl peroxide (BPO), may comprise from 0% to 5% or more of the bead weight. Such beads can be combined with other beads of different sizes and compositions to form the dry component of a surgical cement system. By incorporating the BPO in the beads, the BPO is evenly distributed throughout the cement and produces uniform polymerization. The BPO content of the bead 6 can be carefully controlled within a wide range using the bead forming process discussed later in this specification. The rate of release of the BPO from the bead contributes to the rheological behavior of the cement system.

The bead 6, or another, preferably includes an opacifier 8, such as barium sulphate ($BaSO_4$). By encasing the $BaSO_4$ within the relatively strong bead, the $BaSO_4$ is prevented from forming a stress concentrator in the polymerized cement matrix. Also, the $BaSO_4$ so encased will be uniformly distributed throughout the cement and will produce a uniform radiographic image. The retention of the $BaSO_4$ within the bead contributes to the strength of the polymerized cement.

In one embodiment, the cement dry component comprises beads groupable into different size ranges corresponding to relatively larger beads and relatively smaller beads. Preferably the beads corresponding to the different size ranges have different compositions. Upon being mixed with the liquid component the smaller beads would dissolve more quickly than the larger beads. This would result in any additives contained in the smaller beads being released into the cement matrix and any additive contained in the larger beads tending to be retained in the larger beads. Preferably the smaller beads will completely dissolve before, and thus release their additives before, the larger beads dissolve enough to release their additives to a significant degree. For example, the $BaSO_4$ is preferably incorporated in beads having a size, or maximum dimension, larger than can be dissolved during the working stage so that the $BaSO_4$ is less likely to be freed from the beads and deposited in the polymerizing matrix.

An exemplary cement dry component would contain 85% by weight beads containing $BaSO_4$ and BPO, the beads having an average size of approximately 50 μm. The $BaSO_4$ would be in the form of a fine powder comprising particles approximately 1 μm in size and constituting approximately 8%–12% of the bead weight. The $BASO_4$ may form clumps 8 within the bead 6 as depicted in FIG. 4. The BPO would be in the form of a fine powder comprising particles 7 approximately 1 μm in size and constituting 2%–3% of the bead weight. The remaining 15% by weight of the cement dry component would consist of smaller polymer beads having no additives and an approximate average size of 0.1 μm to 10 μm. Upon being mixed with the liquid component, the smaller beads would dissolve more quickly than the larger beads to form a cement paste. A sufficient amount of BPO would be released from the surface of the larger beads to cause polymerization of the cement while the larger beads remain substantially intact and retain the $BaSO_4$.

An alternate exemplary cement dry component would contain 75% by weight larger beads containing BPO, 10% by weight larger beads containing $BaSO_4$ and 15% by weight smaller beads containing no additives. This alternative composition has manufacturing advantages because only one additive is contained in a particular bead type. This makes the manufacture of the beads simpler. Also, by having the $BaSO_4$ and BPO in different beads, large quantities of each bead type can be made. Cement formulations with different relative percentages of $BaSO_4$ and BPO can then be easily made by mixing different amounts of each bead type.

However, to take full advantage of the present invention, the BPO preferably would all be placed in the smaller beads of the above examples so that the BPO is all available to initiate polymerization upon dissolution of the smaller beads and before the larger beads dissolve. The size of the smaller beads would preferably be adjusted to a size less than 50 μm to produce the desired release rate of the BPO to obtain a desired rheology. For example, a specific amount of BPO contained in very small smaller beads would be released more quickly and cause sooner and more rapid polymerization than would the same amount of BPO contained in larger smaller beads. The larger beads would contain the $BaSO_4$. The size of the larger beads would preferably be greater than or equal to 50 μm so that they would not dissolve when the smaller beads dissolve. Therefore the larger beads will retain the $BaSO_4$.

In another embodiment, the placement of additives in beads can be even more advantageously effected by placing the additives in strata or layers. FIG. 5 depicts a bead having layers 9, 10 and 11 and surface 12. It is particularly advantageous to place an opacifier at the center of the bead and a polymerization initiator located outwardly away from the center. In the case of spherical or cylindrical beads for example, the polymerization initiator would be located radially outward from the center of the bead. By placing the opacifier in the center 11 of the bead, it is well imbedded and there is little chance of it being loosely incorporated into the matrix of the polymerized cement. By placing the polymerization initiator outwardly away from the center of the bead, release of the polymerization initiator and thus polymerization will occur before dissolution of the bead can release the opacifier from the bead. Selective placement of the initiator containing layer and control of the initiator concentration allows tailoring of the time of polymerization onset and of the rate of polymerization.

In one embodiment, the polymerization initiator would be placed on the surface 12 of the bead. Preferably, all of the polymerization initiator contained in the bead would be located at the bead surface. The polymerization initiator would all be immediately available to the cement mixture to cause polymerization to begin immediately and proceed rapidly upon mixing of the dry and liquid cement components.

In another embodiment, the polymerization initiator would be placed within an outer layer of the bead extending from the surface of the bead into the bead. The polymerization initiator would become available to the cement mixture as this outer layer of the bead dissolves. This more gradual release of the polymerization initiator would result in more gradual polymerization.

In yet another embodiment, the polymerization initiator would be placed in a layer 10 deeper into the bead with a polymer barrier layer 9 surrounding the polymerization initiator containing layer to provide a cement with a specific time delay before polymerization begins. This time delay would be the time required for the barrier layer 9 to dissolve and expose the polymerization initiator containing layer 10.

Finally, the polymerization initiator could be concentrated in a narrow layer in order to produce very rapid polymerization when the layer is exposed because a relatively high concentration of polymerization initiator would be released over the relatively short period of time required to expose all of the narrow layer. Alternatively, the layer could be less concentrated or wider to provide more gradual polymerization because it would take more time for dissolution of the bead to free the polymerization initiator in the wider layer.

The novel layering of the present invention would enable full utilization of all of the BPO contained in the beads since the BPO would be placed in the regions of the bead that will be exposed in use. This is an advantage over previous cement beads which have a polymerization initiator randomly distributed within the beads and therefore only the polymerization initiator that by chance lies within the outer regions of the beads which are dissolved in use is utilized.

Such strategic incorporation of additives can yield specific, desirable rheological behavior and strength characteristics. Likewise, the above structure can advantageously accommodate other additives such as dyes, antibiotics, bone growth factors, and other useful agents.

It is preferable that the polymer or polymer mixture comprising the beads be substantially uniform throughout the bead in order to produce a substantially homogeneous bead containing additives as so far described. In the case of the embodiments having additives in strata, it is preferable for the bead to form a structure having a homogeneous composition of a polymer or polymer mixture and the additives distributed in strata within the homogeneous composition as shown in FIG. 5. The additives can be thought of as located in an orbit within the polymer bead about the center of the bead.

According to the present invention the additives can be placed in beads of specific sizes, they can be placed singly or in combination with other additives, and they can advantageously be placed in strata to achieve precise timing and positive encapsulation. All of these structures can be produced by modifying the process described in U.S. Pat. No. 4,675,140. In this process solid particles or viscous liquid droplets of core material are encapsulated in a coating material by feeding a suspension or solution of the two materials onto a rotating surface.

This modified process, as used in the present invention, advantageously forms beads from a liquified polymer composition containing a liquified polymer and an additive. It is distinguished from other known processes which use a polymerization reaction to form beads. By using a liquified polymer, a broader range of additives can be incorporated. For example, since the polymer is prepolymerized, BPO can be added far in excess of that which can be added in a polymerization reaction and without adverse impact on the molecular weight of the polymer. Also, the process can be controlled to produce a very short dwell time so that the additive is subjected to the solvent or heat used to liquify the polymer for a short time period. This dwell time can be as short as a few seconds or even fractions of a second. Therefore, additives that would otherwise be degraded or dissolved by the solvent or heat may be used. In contrast, in prior art polymerization reactions, any additives would be exposed to the polymerization solution for the entire reaction period which typically can be as long as several hours.

This process also is distinguished from other processes used to form bone cement beads containing additives in that it is a continuous process and it is capable of forming beads having a wide range of controlled sizes. Coated particles and droplets of excess coating material are centrifugally thrown from the perimeter of the rotating surface and solidified by cooling or evaporation. The excess coating material forms dried droplets smaller than the coated particles and can therefore be easily separated and recycled. The continuous and controllable nature of the process and the ease of separating product from recyclable coating material make the process more economical and more efficient than other processes. They also make the process applicable where it is desirable to have only coated particles in the final product. This process is capable of coating particles ranging from 1 µm to 500 µm and can produce finished beads in a variety of specific sizes as needed.

In the instant invention, a bead as shown in FIG. 4 can be made by the above process by liquefying a polymer, such as by dissolving it in a solvent or melting it, and suspending or dissolving the desired additive or additives in the liquid and then feeding the suspension or solution to the rotating surface. In the preferred embodiment, bulk polymethylmethacrylate (PMMA) homopolymer or polymethylmethacrylate styrene (PMMAS) co-polymer with no or minimal residual BPO, and a molecular weight of at least 100,000 is dissolved in an organic solvent such as acetone, methylene chloride, or other known organic solvent. BPO, typically in the form of a fine powder, is dissolved (or suspended depending on the solvent used) in the polymer solution. Since the beads are formed directly from a polymer rather than in a polymerization reaction, any desirable BPO concentration can be achieved without affecting the molecular weight of the polymer. In addition $BaSO_4$ may be suspended in the solution. The suspension is fed to the rotating atomization equipment where centrifugal force causes the suspension to atomize when it leaves the rotating surface. In the preferred embodiment the process is used to form a batch of larger beads containing $BaSO_4$ and a batch of smaller beads containing BPO. These are then combined in the cement dry component in the desired amounts.

The pure polymer beads formed from excess coating material can be recycled or incorporated as fine beads into the dry component of the cement system to provide desired properties. The process can also be run without any additives to produce only pure polymer beads for incorporation into the dry component. Other additives that can be advantageously placed in beads include dyes, antibiotics, bone growth factors, and other pharmacological or therapeutic agents. This process is particularly suited to incorporating fragile pharmacological agents because of the potential for a very short dwell time of the additive in solution and the ability to conduct the process at low temperatures.

A layered bead as shown in FIG. 5 can be produced by iteratively using the beads from a prior coating step as the particles in subsequent coating steps. For example, a bead having $BaSO_4$ encapsulated at its center surrounded by a concentrated band of BPO and an outer barrier layer of pure PMMA can be produced by the following steps. A first bead containing $BaSO_4$ is produced by solidifying a first liquified polymer composition containing liquified PMMA and $BaSO_4$. This first bead is then suspended in a solution containing BPO, such as BPO dissolved in methanol. (The first bead is not soluble in methanol. However, it is possible to use the process of this invention to coat a bead soluble in the solution since the dwell time can be made to be so short as to prevent dissolution of the bead.) The process is carried out to yield a second bead comprising $BaSO_4$ encapsulated in PMMA, the second bead being coated with BPO. The process is repeated with a PMMA solution to apply the final PMMA outer layer.

A wider, less concentrated, BPO containing layer could be produced by coating the first beads with a more viscous liquid containing BPO, such as liquified PMMA containing BPO, rather than BPO dissolved in methanol.

A cement system having a dry component comprising these beads in an appropriate mix with small beads will have the highly desirable properties of a controlled time delay until the onset of polymerization (time to dissolve through outer layer of PMMA) followed by rapid polymerization as the concentrated layer of BPO becomes available. FIG. 6 depicts the fully polymerized cement. The beads 13 will be securely incorporated in the polymer matrix 14 since polymerization initiates from the beads. The $BaSO_4$ 15 will be securely held in the bead centers where it cannot weaken the cement and where it will be uniformly distributed with the beads throughout the hardened cement to yield a uniform radiographic image.

Beads according to the present invention having various compositions and properties can be produced by repeating the above steps using the beads from prior steps with different liquid compositions to form a desired bead with stratified additives.

The present invention provides for careful tailoring of the rheological properties of bone cements and for improvement in the strength of bone cements. The rheological advantages of the present invention can be best understood by referring to FIG. 7 which depicts several exemplary viscosity versus time curves obtainable by the inventive cements described above. These curves range from immediate, rapid polymerization to delayed progressive polymerization. For example, curve 1 represents a cement that begins to polymerize immediately and continues to harden very rapidly. This type of curve would result from a cement having a high concentration of a polymerization initiator in small readily dissolved beads whereby the polymerization initiator would all be rapidly released by dissolution of the small beads during mixing. Curve 1 would also result from a bead having a surface coated with a polymerization initiator.

Curve 2 represents a cement that begins to polymerize during mixing and continues to polymerize at a gradually increasing rate. This curve would result from a bead having a polymerization initiator dispersed throughout the bead so that some polymerization initiator is exposed immediately and as more of the bead dissolves, more polymerization initiator becomes available. Curve 2 would also result from a bead having a relatively thick outer layer containing polymerization initiator. The polymerization initiator would be released gradually, starting immediately during mixing, as the outer layer dissolves.

Curve 3 represents a cement having a delay $t_1$ before polymerization begins and then continued polymerization at a gradually increasing rate. This curve would result from a layered bead having an outer layer containing no polymerization initiator and a relatively wide inner layer containing polymerization initiator so that once the outer layer is dissolved, the polymerization initiator begins to be gradually released. Such a time delay is advantageous where a longer working time is desirable or where the operating environment is excessively warm which would lead to accelerated polymerization.

Curve 4 represents a cement having a relatively long delay $t_2$ before polymerization begins and then rapid polymerization. This curve would result from a layered bead structure having a thick outer layer with no polymerization initiator and then a very concentrated band of polymerization initiator which is released quickly upon dissolution of the outer layer.

Finally, curve 5 represents a cement having a long delay and more gradual polymerization. This would result from a layered bead structure having a thick outer layer with no polymerization initiator and a wide polymerization initiator containing inner layer that would gradually release the polymerization initiator.

While the foregoing has described exemplary embodiments of the present invention, further variations are possible. For example, many other desirable polymerization curves could be obtained using the techniques of this invention. Also, particle sizes may vary depending on the particular additive employed and its source. Likewise, the beads may be any appropriate shape including but not limited to spheres, discs, flakes, rods and irregular or rough spheroids. With regard to the embodiments of the present invention containing strata of additives, the additives are conveniently located with reference to the center of the bead. For example, with spherical or cylindrical beads, the strata are located radially outwardly away from the center of the bead. Spherical beads are preferred because they result in easier mixing of the cement mixture and because they are the natural shape produced by the preferred bead forming process of the present invention. Finally, the embodiment of the present invention using bead size to control release and retention of additives could be combined with the embodiment using layering. An exemplary dry component would have larger beads with an opacifier located at the center of the beads and smaller beads containing a polymerization initiator that would be released by dissolution of the smaller beads.

With regard to the embodiments of the present invention wherein additives are placed in beads of a particular size, the size may be measured in terms of diameter, mass, volume or another appropriate measure that will yield the selective retention and release of additives of the present invention. Preferably, the size is measured in terms of the bead diameter or maximum dimension. Also, the smaller beads may be of a different shape than the larger beads. For example, the smaller beads may comprise flake polymer or milled beads to facilitate dissolution of the smaller beads. Likewise, the order, thickness, and concentration of layers in a layered bead structure will be varied to suit a particular application and produce desired properties. In addition, the cement may comprise a polymer or combination of polymers different from those used in the examples. However, it will be understood by those skilled in the art that these modifications and others may be made without departing from the spirit and scope of the invention defined by the appended claims.

What is claimed is:

1. A bone cement having a dry component and a liquid component, the dry component comprising:
   polymer beads, at least some of the beads containing a first additive and at least some of the beads containing a second additive;
   means for selectively retaining the first additive within beads containing the first additive; and
   means for selectively releasing the second additive from beads containing the second additive.

2. A bone cement having a dry component and a liquid component, the dry component comprising:
   a polymer bead, the bead having a center and the bead having an exterior surface the polymer composition of the bead being uniform throughout the bead;
   an additive associated with the polymer bead, the additive comprising a plurality of particles contained within a stratum located relative to the center of the bead, the stratum of particles comprising a volume less than the entire bead volume, the stratum being located between the center of the bead and the exterior surface such that a first portion of the bead, which corresponds to the stratum, contains the additive particles and a second portion of the bead lacks the additive particles.

3. The bone cement of claim 2 wherein the additive is a polymerization initiator and the stratum extends from the bead surface part way into the bead, such that the first portion containing the additive is near the surface of the bead and the second portion lacking the additive is near the center of the bead.

4. The bone cement of claim 2 wherein the additive is an opacifier and the stratum is located near the center of the bead such that the first portion containing the additive is near the center of the bead and the second portion lacking the additive is near the surface of the bead.

5. A bone cement having a dry component and a liquid component, the dry component comprising:
   a polymer bead; and
   an additive associated with the polymer bead, the additive being located in an inner stratum located relative to the center of the bead wherein the additive is a polymerization initiator and the bead further includes an outer layer which lacks the additive, the outer layer surrounding the inner stratum such that the polymerization initiator is released after the dissolution of the outer layer by the liquid component upon combining the dry component and liquid component.

6. The bone cement of claim 2 wherein the additive is selected from the group consisting of opacifiers, polymerization initiators, dyes, antibiotics, and bone growth factors.

7. A bone cement comprising a dry component and a liquid component, the dry component including relatively larger polymer beads and relatively smaller polymer beads, the composition of the relatively smaller polymer beads being different from the composition of the relatively larger polymer beads, the relatively smaller polymer beads dissolving in the liquid component before the relatively larger polymer beads dissolve in the liquid component when the dry and liquid components are mixed.

8. The bone cement of claim 7 further including an opacifier incorporated within the relatively larger polymer beads.

9. The bone cement of claim 7 wherein the relatively larger polymer beads have an average size greater than approximately 50 µm and the relatively smaller polymer beads have an average size smaller than approximately 50 µm.

10. The bone cement of claim 7 further including a polymerization initiator incorporated within the relatively smaller polymer beads.

11. The bone cement of claim 7 wherein the dry component consists of approximately 85% by weight relatively larger polymer beads and approximately 15% by weight relatively smaller polymer beads, the relatively larger polymer beads containing an opacifier and a polymerization initiator, the relatively larger polymer beads having an average size of at least 50 µm and the relatively smaller polymer beads having an average size of less than 10 µm.

* * * * *